US00PP31738P2

(12) United States Plant Patent
Oudshoorn

(10) Patent No.: US PP31,738 P2
(45) Date of Patent: May 5, 2020

(54) ***MONARDA* PLANT NAMED 'DOMONPOCRE'**

(50) Latin Name: *Monarda didyma*
Varietal Denomination: Domonpocre

(71) Applicant: DUMMEN GROUP B.V., De Lier (NL)

(72) Inventor: Herbert Oudshoorn, Rijpwetering (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/350,648

(22) Filed: Dec. 14, 2018

(51) Int. Cl.
*A01H 5/02* (2018.01)
*A01H 6/50* (2018.01)

(52) U.S. Cl.
USPC ..... Plt./455

(58) Field of Classification Search
USPC ..... Plt./263.1, 455
See application file for complete search history.

(56) References Cited

PUBLICATIONS

Dummen Orange Perennials 2016-2017 catalog (https://issuu.com/bepplersrl/docs/dummen_perennials_2017). 4 pages. (Year: 2017).*

* cited by examiner

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Monarda* plant named 'Domonpocre', characterized by its upright plant habit; freely branching habit; dark green-colored leaves; freely flowering habit; large inflorescences with light red purple-colored flowers; and relative tolerance to Powdery Mildew.

1 Drawing Sheet

Botanical designation: *Monarda didyma.*
Cultivar denomination: 'DOMONPOCRE'.

BACKGROUND OF THE INVENTION

The present invention relates to a new and distinct cultivar of *Monarda* plant, botanically known as *Monarda didyma*, typically grown a container plant and hereinafter referred to by the name 'Domonpocre'.

The new *Monarda* plant is a product of a planned breeding program conducted by the Inventor in Aalsmeer, The Netherlands. The objective of the breeding program is to create new compact and freely branching *Monarda* plants with numerous attractive flowers.

The new *Monarda* plant originated from a cross-pollination in 2009 of *Monarda didyma* 'Pink Lace', disclosed in U.S. Plant Pat. No. 18,367, as the female, or seed, parent with *Monarda didyma* 'Cambridge Scarlet', not patented, as the male, or pollen, parent. The new *Monarda* plant was discovered and selected by the Inventor as a single flowering plant from within the progeny of the stated cross-pollination grown in a controlled environment in Aalsmeer, The Netherlands in 2010.

Asexual reproduction of the new *Monarda* plant by vegetative terminal cuttings in Aalsmeer, The Netherlands, since 2011 has shown that the unique features of this new *Monarda* plant are stable and reproduced true to type in successive generations.

SUMMARY OF THE INVENTION

Plants of the new *Monarda* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Domonpocre'. These characteristics in combination distinguish 'Domonpocre' as a new and distinct *Monarda* plant:

1. Upright plant habit.
2. Freely branching habit.
3. Dark green-colored leaves.
4. Freely flowering habit.
5. Large inflorescences with light red purple-colored flowers.
6. Relatively tolerant to Powdery Mildew.

Plants of the new *Monarda* differ primarily from plants of the female parent, 'Pink Lace', in the following characteristics:

1. Plants of the new *Monarda* are more freely branching than plants of 'Pink Lace'.
2. Plants of the new *Monarda* are more tolerant to Powdery Mildew than plants of 'Pink Lace'.

Plants of the new *Monarda* differ primarily from plants of the male parent, 'Cambridge Scarlet', in the following characteristics:

1. Plants of the new *Monarda* are more freely branching than plants of 'Cambridge Scarlet'.
2. Plants of the new *Monarda* are more tolerant to Powdery Mildew than plants of 'Cambridge Scarlet'.

Plants of the new *Monarda* can be compared to plants of *Monarda didyma* 'Sugar Lace', disclosed in U.S. Plant Pat. No. 22,918. In side-by-side comparisons, plants of the new *Monarda* differ primarily from plants of 'Sugar Lace' in the following characteristics:

1. Plants of the new *Monarda* are more compact than plants of 'Sugar Lace'.
2. Plants of the new *Monarda* have thicker lateral branches than plants of 'Sugar Lace'.
3. Plants of the new *Monarda* have larger leaves than plants of 'Sugar Lace'.
4. Plants of the new *Monarda* have slightly darker red purple-colored flowers than plants of 'Sugar Lace'.

BRIEF DESCRIPTION OF THE PHOTOGRAPH

The accompanying colored photograph illustrates the overall appearance of the new *Monarda* plant showing the colors as true as it is reasonably possible to obtain in colored reproductions of this type. Colors in the photographs may differ slightly from the color values cited in the detailed botanical description which accurately describe the actual colors of the new *Monarda* plant.

The photograph is a side perspective view of a typical flowering plant of 'Domonpocre' grown in a container.

DETAILED BOTANICAL DESCRIPTION

The aforementioned photograph and following observations, measurements and values describe plants grown during the summer in 13-cm containers in an outdoor nursery in Aalsmeer, The Netherlands and under cultural practices typical of commercial *Monarda* production. During the production of the plants, day temperatures averaged 20° C. and night temperatures averaged 16° C. Plants were pinched one time after planting young plants and were four months old when the photograph was taken and 25 weeks when the description was taken. In the detailed description, color references are made to The Royal Horticultural Society Colour Chart, 2015 Edition, except where general terms of ordinary dictionary significance are used.

Botanical classification: *Monarda didyma* 'Domonpocre'.

Parentage:

*Female, or seed, parent.*—*Monarda didyma* 'Pink Lace', disclosed in U.S. Plant Pat. No. 18,367.

*Male, or pollen, parent.*—*Monarda didyma* 'Cambridge Scarlet', not patented.

Propagation:

*Type cutting.*—By terminal vegetative cuttings.

*Time to initiate roots, summer.*—About ten days at temperatures about 26° C.

*Time to initiate roots, winter.*—About two weeks at temperatures about 23° C.

*Additional time to produce a rooted young plant, summer.*—About 12 days at temperatures about 23° C.

*Additional time to produce a rooted young plant, winter.*—About 16 days at temperatures about 18° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Moderately freely branching; dense.

Plant description:

*Plant and growth habit.*—Herbaceous perennial; upright plant habit; moderately vigorous growth habit; rapid growth rate.

*Plant height.*—About 32 cm.

*Plant width.*—About 30 cm.

*Lateral branch description.*—Branching habit: Freely basal branching habit with about six to eight main stems. Length: About 18 cm to 20 cm. Diameter: About 4 mm. Internode length: About 3 cm to 5 cm. Strength: Strong. Aspect: Mostly upright. Texture: Pubescent. Color: Close to 146C.

Leaf description:

*Arrangement.*—Opposite, simple.

*Length.*—About 9 cm to 10 cm.

*Width.*—About 4.5 cm.

*Shape.*—Ovate.

*Apex.*—Acute.

*Base.*—Obtuse.

*Margin.*—Serrate.

*Texture, upper and lower surfaces.*—Pubescent and slightly rugose.

*Venation pattern.*—Pinnate.

*Color.*—Developing and fully developed leaves, upper surface: Close to 137A; venation, close to 147C. Developing and fully developed leaves, lower surface: Close to 137C; venation, close to 148C.

*Petioles.*—Length: About 1.3 cm. Diameter: About 3 mm. Strength: Moderately strong. Texture, upper and lower surfaces: Pubescent. Color, upper and lower surfaces: Close to 145B.

Flower description:

*Flower form, arrangement and flowering habit.*—Single labiate flowers arranged in large terminal globular spikes; flowers sessile; flowers face upright to outwardly; freely flowering habit with about 30 flowers developing per inflorescence and about 2,500 flowers developing per plant during the flowering season.

*Natural flowering season.*—Plants flower during August and September in The Netherlands; plants begin flowering about 16 weeks after planting.

*Postproduction longevity.*—Flowers maintain good substance for about one week on the plant; flowers not persistent.

*Fragrance.*—Moderate to strongly fragrant; pleasant, spicy.

*Flower buds.*—Length: About 1.2 cm. Diameter: About 2 mm. Shape: Narrowly oblanceolate. Color: Close to 64A.

*Inflorescence height.*—About 5 cm to 6 cm.

*Inflorescence diameter.*—About 5 cm to 6 cm.

*Flower diameter.*—About 6 mm.

*Flower depth (height).*—About 3.2 cm.

*Petals.*—Arrangement: Labiate; upper lip hooded; lower lip, a single lobe; lips fused proximally. Length, upper and lower lips: About 1.5 cm. Width, upper lip: About 1 mm. Width, lower lip: About 5 mm. Shape, upper lip: Lanceolate; apex, acute. Shape, lower lip: Oblanceolate; apex, aristate. Margin, upper and lower lips: Entire. Texture, upper and lower lips, upper surface: Smooth, glabrous. Texture, upper and lower lips, lower surface: Pubescent. Color, upper and lower lips: When opening, upper and lower surfaces: Close to 60B. Fully opened, upper surface: Close to 63A; color does not change with development. Fully opened, lower surface: Close to 61B; color does not change with development.

*Sepals.*—Quantity and arrangement: Five in a single whorl; proximally fused into a tubular calyx. Length: About 1 cm. Width: About 1 mm. Apex: Acuminate. Margin: Free parts, entire. Texture, upper and lower surfaces: Pubescent. Color, when opening and fully opened, upper and lower surfaces: Close to 147C, distally, close to 187A.

*Peduncles*.—Length: About 14 cm to 28 cm. Diameter: About 4 mm. Strength: Strong. Aspect: About 25° to 30° from vertical. Texture: Pubescent. Color: Close to 146C.

*Reproductive organs*.—Stamens: Quantity per flower: Two. Filament length: About 1.3 cm. Filament color: Close to 63B. Anther length: About 2 mm. Anther shape: Elliptical; dorsifixed. Anther color: Close to 77A. Pollen amount: Moderate. Pollen color: Close to 8B. Pistils: Quantity per flower: One. Pistil length: About 3 cm. Stigma shape: Cleft, unequal. Stigma color: Close to 77A. Style length: About 2.9 cm. Style color: Proximally, close to 155A; distally, close to 77B. Ovary color: Close to 11C.

*Seed and fruit*.—To date, seed and fruit production have not been observed on plants of the new *Monarda*.

Pathogen & pest resistance: Plants of the new *Monarda* have been observed to be relatively tolerant to Powdery Mildew (*Erysiphe cichoracearum*). Plants of the new *Monarda* have not been observed to be resistant to pests and other pathogens common to *Monarda* plants.

Garden performance: Plants of the new *Monarda* have exhibited good tolerance to rain, wind and temperatures ranging from about −20° C. to 30° C.

It is claimed:

1. A new and distinct *Monarda* plant named 'Domonpocre' as illustrated and described.

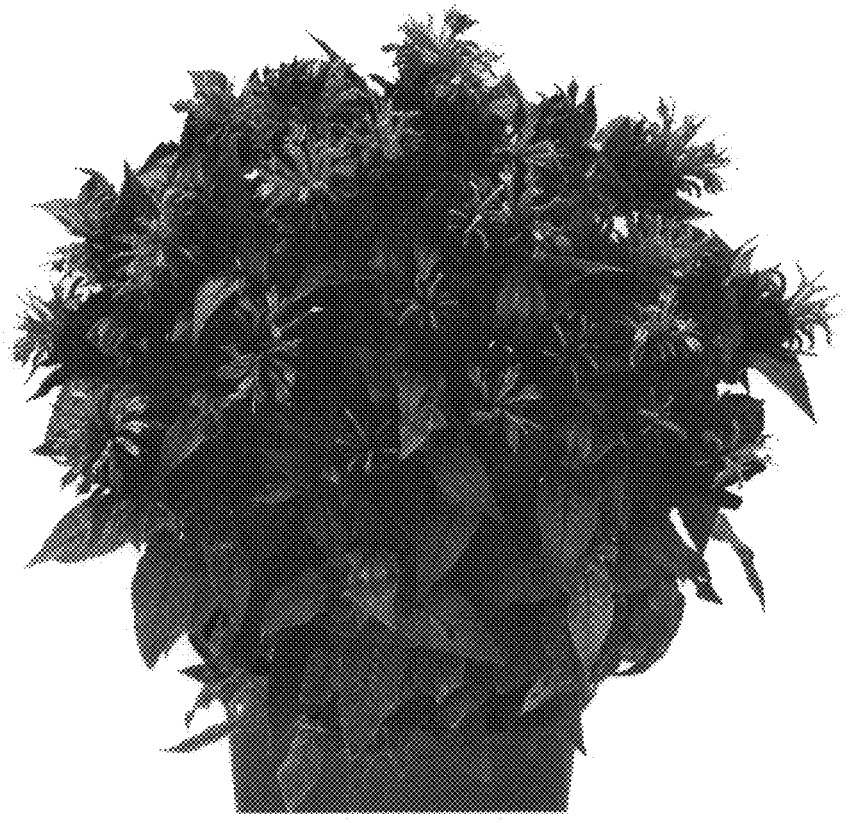

* * * * *